US00PP34739P3

(12) United States Plant Patent
Brown

(10) Patent No.: US PP34,739 P3
(45) Date of Patent: Nov. 15, 2022

(54) ***CALLISTEMON* PLANT NAMED 'CNU01'**

(50) Latin Name: *Callistemon citirinus*
Varietal Denomination: CNU01

(71) Applicant: Nuflora International Pty Ltd, Macquarie Fields (AU)

(72) Inventor: Graham Brown, Bowral (AU)

( * ) Notice: Subject to any disclaimer, the term of this patent is extended or adjusted under 35 U.S.C. 154(b) by 3 days.

(21) Appl. No.: 17/803,225

(22) Filed: Mar. 21, 2022

(65) Prior Publication Data

US 2022/0304206 P1 Sep. 22, 2022

Related U.S. Application Data

(60) Provisional application No. 63/163,812, filed on Mar. 20, 2021.

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Samuel R. McCoy, Jr.

(57) ABSTRACT

A new and distinct variety of *Callistemon* plant named 'CNU01' which is characterized by the combination of an upright growth habit, an abundance of relatively small leaves, oblong inflorescence comprised of an abundance of white flowers, and the stability of all characteristics from generation to generation.

2 Drawing Sheets

Latin name of the genus and species: The Latin name of the genus and species of the novel variety disclosed herein is *Callistemon citrinus.*

Variety denomination: The inventive variety of *Callistemon* disclosed herein has been given the variety denomination 'CNU01'.

BACKGROUND OF THE INVENTION

Parentage: 'CNU01' is the result of a controlled cross-pollination breeding program carried out by the inventor at a commercial plant breeding facility in Cobbitty, New South Wales, Australia in October of 2014. The inventor performed a controlled cross-pollination of the seed parent, *Callistemon* 'Hot Pink' (South African Plant Breeder's Rights grant number ZA 20043189) with *Callistemon* 'Mauve Mist' (unpatented), the pollen parent. The resulting seedlings were grown for two years to evaluate for new and distinct characteristics. In October of 2016, the inventor selected the new *Callistemon* plant for its compact, upright growth habit and white flowers. This new and distinctive cultivar was given the name 'CNU01'

Asexual Reproduction: Asexual reproduction of 'CNU01', by way of stem cuttings, was first initiated in 2016 in Cobbitty, New South Wales, Australia. Through greater than four subsequent generations of asexual propagation, the unique features of this cultivar have proven to be stable and true to type.

SUMMARY OF THE INVENTION

The cultivar 'CNU01' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'CNU01'. These characteristics in combination distinguish 'CNU01' as a new and distinct *Callistemon* cultivar:

1. *Callistemon* 'CNU01' exhibits a compact, upright growth habit; and
2. *Callistemon* 'CNU01' exhibits an abundance of relatively small leaves; and
3. *Callistemon* 'CNU01' exhibits cylindrical inflorescences with an abundance of white flowers; and
4. *Callistemon* 'CNU01' exhibits flowers with white exserted stamens.

BOTANICAL DESCRIPTION OF THE PLANT

Figure 1:
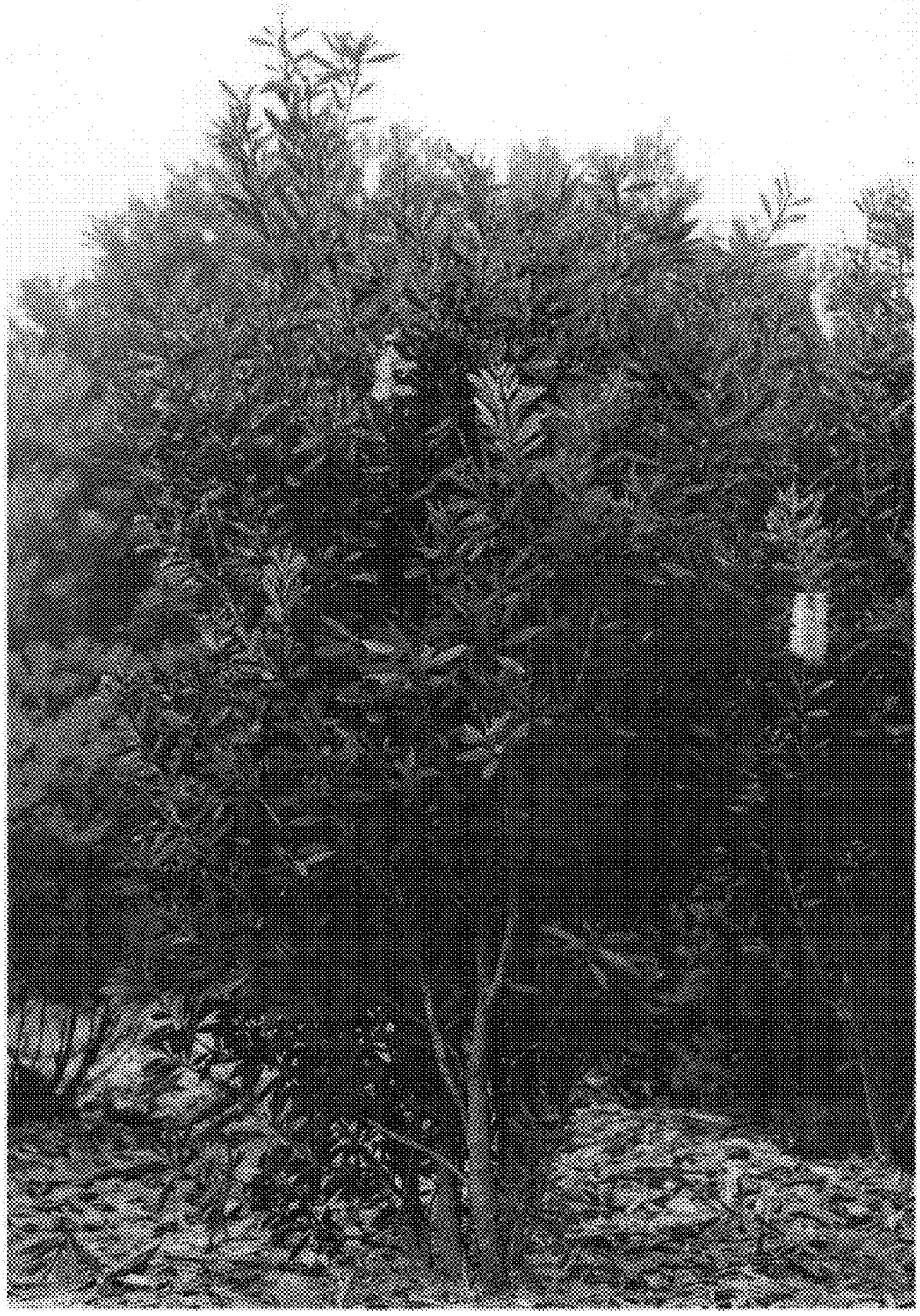
FIG. 1 illustrates, as nearly true as it is reasonably possible to make the same in color photographs of this type, an exemplary plant of 'CNU01'. This plant is approximately 36 months old.
Figure 2:
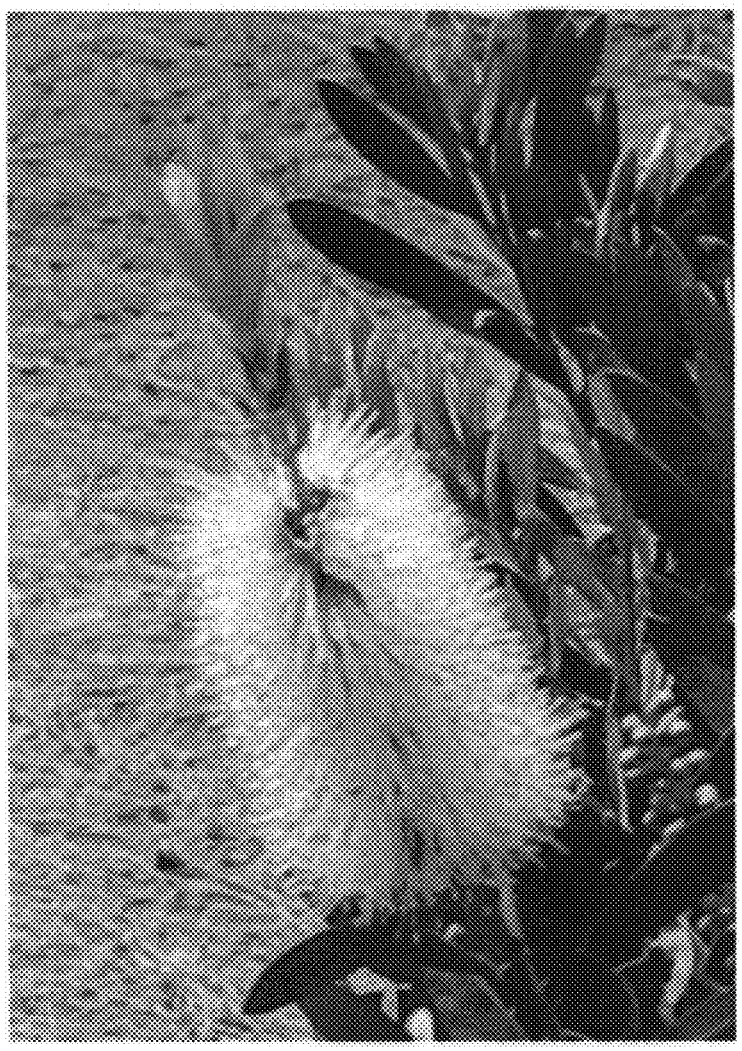
FIG. 2 illustrates, as nearly true as it is reasonably possible to make the same in color photographs of this type, the typical inflorescence of 'CNU01'.

The following observations and measurements were made in May of 2022 and describe a 6-year-old 'CNU01' plant grown in the ground in Clarendon, New South Wales, Australia. The plant was allowed to grow with full sun exposure and maintained with sporadic overhead irrigation during prolonged drought conditions and slow-release granular fertilizer applications. The plant received a light prune, biannually. No pest or disease control measures were utilized in production.

Those skilled in the art will appreciate that certain characteristics will vary with older or, conversely, with younger plants. 'CNU19' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The *Royal Horticultural Society Colour Chart*, The Royal Horticultural Society, London, 1986 (third edition).

A botanical description on 'CNU01', comparisons with the parents, comparisons with sibling cultivars, and a comparison with the most similar variety of common knowledge are provided below.

*General plant description*—

*Growth habit*—Evergreen shrub with a semi-compact, globular growth habit.

*Plant Profile*—Rotund.

*Height*—180 cm from the soil level to the top of the foliar plane.

*Plant spread*—130 cm.

*Growth rate*—Moderately fast.

*Plant vigor*—Moderately vigorous.

*Propagation type*—Stem cuttings.

*Time to produce a rooted cutting*—Approximately 120 days to produce a rooted cutting at approximately 25 degrees Celsius.

*Time to produce a finished plant*—32 weeks to produce a fully rotted 15 cm container.

*Disease resistance*—Neither resistance nor susceptibility to typical *Callistemon* pests and diseases has been observed.

*Environmental tolerances*—Adapt to, at least, USDA Zones 9 through 11; moderate tolerance to rain; moderate to high tolerance to wind; drought tolerant once established.

*Root system*—

*General*—Moderately dense and freely branched rooting; roots are moderately fibrous.

*Distribution in the soil profile*—Shallow to moderately deep.

*Stem*—

*General branching habit*—A single main stem, freely branching from the base, with an abundance of lateral branches.

*Quantity of main stems per plant*—1.

*Diameter of the main stem*—12.0 cm at soil level.

*Abundance of lateral branches*—Abundant.

*Length of lateral branches*—Approximately 88 cm.

*Diameter of lateral branches*—Approximately 0.9 cm.

*Internode length*—0.5 cm, on average.

*Attitude of lateral branches*—Upright and outward, at an acute angle to the main stem.

*Aspect*—Rounded.

*Texture, juvenile*—Tomentose.

*Texture, mature and oldest wood*—Glabrous and becoming progressively fissured and furrowed with age, followed by exfoliation of the outer bark in small segments, revealing yet more fissured and furrowed bark beneath.

*Luster*—Slightly glossy to matte.

*Strength*—Strong.

*Color, juvenile lateral branches*—Yellow-green, nearest to RHS 154A, and heavily suffused with greyed-orange, nearest to RHS 171D; as stems mature, they become progressively suffused with greyed-orange, nearest to RHS 163C.

*Color, mature lateral branches*—Greyed-orange, distally, nearest to a combination of 166B and 163D yet predominantly colored 166B; transitioning to greyed-white near the proximal end of the stem, RHS 196B.

*Color, main stem and oldest wood of lateral branches*—Exfoliating bark is a combination of greyed-green and grey-brown, nearest to RHS 197B and 199C; exposed wood below the exfoliating bark is greyed-orange, nearest to a combination of RHD 164A, 164B, 164C, and 165B.

*Foliage*—

*Arrangement*—Whorled.

*Division*—Simple.

*Attachment*—Petiolate.

*Attitude*—Upward and outward.

*Lamina*—

*Shape*—Narrowly lanceolate.

*Aspect*—Flat.

*Dimensions*—7.0 cm long and 1.3 cm wide.

*Apex*—Acute with a very short, soft mucronate tip.

*Base*—Cuneate.

*Margin*—Entire; not undulated.

*Texture of the juvenile foliage, adaxial surface*—Tomentose.

*Texture of the juvenile foliage, abaxial surface*—Tomentose.

*Texture of the mature foliage, adaxial surface*—Coriaceous; glabrous.

*Texture of the mature foliage, abaxial surface*—Coriaceous; glabrous.

*Luster of the juvenile foliage, adaxial surface*—Matte.

*Luster of the juvenile foliage, adaxial surface*—Matte.

*Texture of the mature foliage, abaxial surface*—Slightly glossy.

*Texture of the mature foliage, abaxial surface*—Matte to slightly glossy.

*Color*—

*Juvenile foliage, adaxial surface*—Greyed-orange, nearest to in between RHS 171B and 171C. Lamina becomes progressively suffused with yellow-green, RHS 147B, with age.

*Juvenile foliage, abaxial surface*—Greyed-orange, nearest to in between RHS 171B and 171 C. Lamina becomes progressively suffused with yellow-green, RHS 147C, with age.

*Mature foliage, adaxial surface*—Yellow-green, nearest to RHS 147A.

*Mature foliage, abaxial surface*—Yellow-green, nearest to RHS 147B.

*Venation*—

*Pattern*—Pinnate.

*Color, adaxial surface*—Same as the surrounding foliage; nearest to in between green and yellow-green, RHS 137A and 147A.

*Color, adaxial surface*—Same as the surrounding foliage; green, nearest to in between RHS 137B and 137C.

*Petiole*—

*Length*—0.25 cm.

*Diameter*—0.15 cm at the base.

*Strength*—Strong.

*Texture, juvenile*—Tomentose.

*Texture, mature*—Smooth; glabrous.

*Luster, juvenile*—Matte.

*Luster, mature*—Slightly glossy.

*Color, adaxial and abaxial surfaces*—Juvenile petioles are greyed-red, nearest to RHS 180B, and suffused with yellow-green near the base, RHS 151A. Mature petioles are yellow-green, nearest the RHS 151A.

*Stipules*—None observed.
*Inflorescence*—
*Habit*—Terminal leafy spikes, borne directly on the lateral branches.
*Natural flowering season*—Heaviest bloom period is spring, with sporadic flowering through summer and a second larger flush of blooms in autumn, in Zone 9 of the United States.
*Time to flower or response time*—Approximately 6 months.
*Dimensions*—Average of 6.5 cm long and 4.0 cm in diameter.
*Quantity of flowers per inflorescence*—30 to 35 flowers.
*Peduncles*—None.
*Flower buds*—
*Shape*—Broad oblong to obovoid.
*Length*—8.0 mm.
*Diameter*—4.5 mm.
*Texture*—Coriaceous; proximal end at the calyx tube is tomentose and distal end at the flower petals is glabrous.
*Luster*—Slightly glossy.
*Color*—Yellow-green, nearest to RHS 145A, and fading lighter towards the apex, nearest to RHS 145C; immature sepal lobes are suffused with red-purple, nearest to RHS 61B.
*Flower*—
*Shape, type*—Rotate, with a single whorl of petals.
*Attachment*—Sessile.
*Flowering habit*—Freely flowering.
*Attitude*—Upright to outward.
*Flower longevity on plant*—Approximately 7 to 10 days.
*Persistent or self-cleaning*—Self-cleaning.
*Fragrance*—Non-fragrant.
*Diameter*—Diameter of the corolla is 11.5 mm; the width across the exserted stamens at their distal end is 15.0 mm.
*Depth*—Depth of the corolla, including the exserted stamens, is 20.0 mm.
*Pedicels*—None; flowers are sessile.
*Calyx*—
*Shape*—Campanulate with sepal lobes adpressed to the corolla at anthesis.
*Length*—4.5 mm, including the sepal lobes.
*Diameter*—3.5 mm, distally, at the sepal lobes.
*Color of the calyx tube*—Yellow-green, nearest to in between RHS 143C and 144A.
*Sepal lobes*—
*Quantity*—5.
*Shape*—Deltoid.
*Dimensions*—1.25 mm long and 1.8 mm wide at the base.
*Apex*—Obtuse.
*Base*—Fused to the calyx tube.
*Margin*—Entire.
*Texture*—Tomentose.
*Luster*—Matte.
*Color*—Yellow-green, nearest to in between RHS 144B and 144C, and suffused with red-purple, nearest to RHS 61B.
*Petals*—
*Quantity*—5.
*Arrangement*—Rotate.
*Length*—3.25 mm.
*Width*—3.0 mm.
*Shape*—Near orbicular.
*Apex*—Obtuse.
*Base*—Truncate.
*Margin*—Entire; light undulation.
*Texture, inner surface*—Glabrous; coriaceous.
*Texture, outer surface*—Glabrous; coriaceous.
*Petal color*—
*When opening, inner surface*—Yellow-green, nearest to RHS 154D.
*When opening, outer surface*—Yellow-green, nearest to RHS 154C.
*Fully opened, inner surface*—Yellow-green, nearest to RHS 154D.
*Fully opened, outer surface*—Yellow-green, nearest to RHS 154C.
*Petal venation color*—No venation is visible.
*Reproductive Organs*—
*Androecium*—
*Stamens*—
*Quantity*—40, on average.
*Anthers*—
*Attachment*—Dorsifixed.
*Shape*—Oblong.
*Dimensions*—0.75 mm long and 0.5 mm wide.
*Color*—Greyed-yellow, nearest to RHS 161D, with pollen removed.
*Filaments*—
*Length*—13.0 mm, on average.
*Diameter*—0.3 mm.
*Color*—White, RHS 155A.
*Amount of Pollen*—Abundant.
*Pollen color*—Yellow, nearest to RHS 5B.
*Gynoecium*—
*Pistil*—
*Quantity*—One.
*Length*—17.75 mm.
*Style*—
*Length*—17.0 mm, on average.
*Diameter*—0.5 mm at the base.
*Color*—Yellow-green, nearest to in between RHS 154C and 154D.
*Stigma*—
*Shape*—Near globular.
*Length*—0.75 mm.
*Diameter*—0.5 cm.
*Color*—Yellow-green, nearest to RHS 154C, and suffused with yellow-green, RHS 153D.
*Ovary position*—Inferior.
*Seed and fruit*—
Seeds not observed.

Comparisons With the Parent Plants

Plants of the new cultivar 'MACGER001' differ from its seed parent, *Callistemon* 'Hot Pink' (South African Plant Breeder's Rights grant number ZA 20043189), by the characteristics described in Table 1.

TABLE 1

| Characteristic | 'CNU01' | 'Hot Pink' |
|---|---|---|
| General coloration of the stamens. | White. | Red-purple. |

Plants of the new cultivar 'CNU01' may be distinguished from its pollen parent, *Callistemon* 'Mauve Mist' (not patented), by the characteristics described in Table 2.

TABLE 2

| Characteristic | 'CNU01 | 'Mauve Mist' |
|---|---|---|
| General coloration of the stamens. | White. | Purple. |

Comparison With the Most Similar Varieties of Common Knowledge

Plants of the new cultivar 'CNU01' may be distinguished from the most similar known commercial comparator, *Callistemon* 'White Anzac' (unpatented), by the characteristics described in Table 3.

TABLE 3

| Characteristic | 'CNU01' | 'White Anzac' |
|---|---|---|
| Growth habit. | Upright. | Spreading. |
| Plant height. | Taller than 'White Anzac'. | Shorter than 'CNU01' |
| Plant width. | Narrower than 'White Anzac'. | Broader than CNU01'. |

Plants of the new cultivar 'CNU01' may be distinguished from its sibling, *Callistemon citrinus* 'CNU06' (co-pending U.S. patent application Ser. No. 17/803,225), by the characteristics described in Table 4.

TABLE 4

| Characteristic | 'CNU01' | 'CNU06' |
|---|---|---|
| Growth habit. | Compact; globular to near columnar. | Compact; globular. |
| Plant height. | Taller than 'CNU06' | Shorter than 'CNU01'. |
| General coloration of the stamens. | White. | Dark Pink. |

Plants of the new cultivar 'CNU01' may be distinguished from its sibling, *Callistemon citrinus* 'CNU07' (co-pending U.S. patent application Ser. No. 17/803,227), by the characteristics described in Table 5.

TABLE 5

| Characteristic | 'CNU01' | 'CNU07' |
|---|---|---|
| Growth habit. | Compact; globular to near columnar. | Compact; globular. |
| Plant height. | Taller than 'CNU07' | Shorter than 'CNU01'. |
| Plant width. | Narrower than CNU07'. | Broader than 'CNU01'. |
| Inflorescence size. | Larger than 'CNU07' | Smaller than 'CNU01'. |

Plants of the new cultivar 'CNU06' may be distinguished from its sibling, *Callistemon citrinus* 'CNU15' (co-pending U.S. patent application Ser. No. 17/803,224), by the characteristics described in Table 6.

TABLE 6

| Characteristic | 'CNU01' | 'CNU15' |
|---|---|---|
| Growth habit. | Compact; globular to near columnar. | Compact; globular. |
| Plant height. | Taller than 'CNU15'. | Shorter than 'CNU01'. |
| General coloration of the stamens. | White. | Dark Pink. |

Plants of the new cultivar 'CNU01' may be distinguished from its sibling, *Callistemon citrinus* 'CNU19' (co-pending U.S. patent application Ser. No. 17/803,223), by the characteristics described in Table 7.

TABLE 7

| Characteristic | 'CNU01' | 'CNU19' |
|---|---|---|
| Growth habit. | Compact; globular to near columnar. | Semi-compact; globular. |
| Plant height. | Typically shorter than 'CNU19' | Typically taller than 'CNU01'. |
| General coloration of the stamens. | White. | Dark Pink. |

That which is claimed is:

1. A new and distinct variety of *Callistemon* plant named 'CNU01', substantially as described and illustrated herein.

* * * * *